(12) United States Patent
Kanai et al.

(10) Patent No.: US 10,241,092 B2
(45) Date of Patent: Mar. 26, 2019

(54) GAS CHROMATOGRAPH DEVICE

(71) Applicant: SHIMADZU CORPORATION, Kyoto-shi, Kyoto (JP)

(72) Inventors: Masaki Kanai, Kyoto (JP); Satoshi Matsuoka, Kyoto (JP); Masanori Nishino, Kyoto (JP); Takahiro Nishimoto, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 196 days.

(21) Appl. No.: 14/437,863

(22) PCT Filed: Oct. 25, 2012

(86) PCT No.: PCT/JP2012/077616
§ 371 (c)(1),
(2) Date: Apr. 23, 2015

(87) PCT Pub. No.: WO2014/064804
PCT Pub. Date: May 1, 2014

(65) Prior Publication Data
US 2015/0268201 A1 Sep. 24, 2015

(51) Int. Cl.
*G01N 30/30* (2006.01)
*G01N 30/54* (2006.01)
(Continued)

(52) U.S. Cl.
CPC ............ *G01N 30/30* (2013.01); *G01N 30/16* (2013.01); *G01N 30/54* (2013.01); *G01N 30/60* (2013.01); *G01N 2030/3084* (2013.01)

(58) Field of Classification Search
CPC ........ G01N 30/30; G01N 30/16; G01N 30/54; G01N 30/60
See application file for complete search history.

(56) References Cited

U.S. PATENT DOCUMENTS

| 5,663,488 A | 9/1997 | Wang et al. |
| 6,530,260 B1 | 3/2003 | Mustacich et al. |

(Continued)

FOREIGN PATENT DOCUMENTS

| CN | 201273894 Y | 7/2009 |
| JP | 59-77063 U | 5/1984 |
| JP | 8-327620 A | 12/1996 |

OTHER PUBLICATIONS

International Search Report dated Jan. 22, 2013, issued in corresponding Patent Application No. PCT/JP2012/077616 (2 pages).
(Continued)

*Primary Examiner* — Xin Zhong
(74) *Attorney, Agent, or Firm* — Westerman, Hattori, Daniels & Adrian, LLP (57) ABSTRACT

A gas chromatograph includes a column module for independently adjusting the temperature of a separation column. The column module is held by an oven with the separation column being horizontal. The column module includes the separation column for separating a sample gas into components, a column accommodating member accommodating inside the separation column while surrounding the separation column by a heat insulating member, and including a gap between the separation column and the heat insulating member for air to flow along the separation column, and a heater, provided inside the column accommodating member, for heating the separation column by being in direct or indirect contact with the separation column. The column accommodating member includes an air inlet port for introducing external air into the gap between the separation column and the heat insulating member, and an air outlet port for exhausting air in the gap.

7 Claims, 5 Drawing Sheets

(51) Int. Cl.
*G01N 30/16* (2006.01)
*G01N 30/60* (2006.01)

(56) References Cited

U.S. PATENT DOCUMENTS

| | | | |
|---|---|---|---|
| 2005/0199121 A1* | 9/2005 | Crnko | G01N 30/30 |
| | | | 95/87 |
| 2005/0258088 A1* | 11/2005 | Botelho | G01N 30/30 |
| | | | 210/198.2 |
| 2008/0047323 A1 | 2/2008 | Botelho et al. | |
| 2009/0045187 A1* | 2/2009 | Stearns | G05D 23/2401 |
| | | | 219/497 |
| 2012/0085148 A1* | 4/2012 | Amirav | G01N 30/30 |
| | | | 73/23.39 |
| 2013/0139574 A1* | 6/2013 | Staats | G01N 30/30 |
| | | | 73/61.57 |

OTHER PUBLICATIONS

Office Action dated Feb. 27, 2017, issued in counterpart Chinese Application No. 201610227553.X. (9 pages).

\* cited by examiner

GAS CHROMATOGRAPH DEVICE

TECHNICAL FIELD

The present invention relates to a gas chromatograph device provided with a column module for accommodating, and controlling the temperature of, a separation column for separating a gasified sample into components.

BACKGROUND ART

Generally, a conventional gas chromatograph device adopts a method of accommodating a separation column inside an oven provided with a heater and adjusts the temperature of the separation column. A fan is installed inside the oven, and the temperature inside the oven is uniformly heated to adjust the temperature of the separation column by causing the air inside the oven to convect by churning with the fan. At the time of cooling the separation column, external air is injected into the oven by the fan, and the air inside the oven is displaced.

However, with the method described above of controlling the temperature of a separation column by a convection oven, since the heat capacity of the oven is significantly greater compared to the separation column, it is difficult to swiftly raise/lower the temperature of the separation column. There is also a problem in that raising/lowering the temperature of the oven with a high heat capacity increases the power consumption.

To solve the problem described above, adjustment of the temperature of the separation column by direct thermal conduction is proposed. For example, Patent Document 1 discloses configuration of an assembly where a heating wire is wound around a separation column, and temperature control of the separation column is independent of an oven, to thereby reduce the heat capacity of a temperature control target compared to the oven and increase the responsiveness of temperature control.

PRIOR ART DOCUMENTS

Patent Documents

Patent Document 1: U.S. Pat. No. 6,530,260

SUMMARY OF THE INVENTION

Problems to be Solved by the Invention

With the method disclosed in Patent Document 1, there is a problem in that the assembly where a heating wire is wound around a separation column is not shut off from external air, and the separation column is easily affected by the temperature variation of the external air or by convection. This problem may be solved by covering the entire assembly with heat insulating material, but this reduces the heat dissipation efficiency at the time of cooling of the separation column, and swift cooling of the separation column becomes difficult.

Accordingly, the present invention has its aim to enable swift raising/lowering of the temperature of a separation column while preventing the temperature of the separation column from being affected by the temperature variation of external air or by convection.

Solutions to the Problems

A gas chromatograph device according to the present invention includes a column module including a separation column for separating a sample gas into components, a column accommodating member accommodating inside the separation column while surrounding the separation column by a heat insulating member, and including a gap between the separation column and the heat insulating member for air to flow along the separation column, a heater, provided inside the column accommodating member, for heating the separation column by being in direct or indirect contact with the separation column, an air inlet port, provided to the column accommodating member, for introducing external air into the gap, and an air outlet port, provided to the column accommodating member, at a position different from the air inlet port, for exhausting air in the gap, a sample injection part for injecting a sample gas into the separation column of the column module, a detector for detecting a sample component separated by the separation column, an oven accommodating flow channels for connecting, respectively, the sample injection part and the separation column, and the detector and the separation column, the oven being for adjusting an internal temperature to a constant temperature, where the column module is held by the oven with the separation column horizontally arranged.

Effects of the Invention

According to the gas chromatograph device of the present invention, the column module is held by the oven in a state where the separation column is horizontally arranged, and thus, the temperature of the separation column may be adjusted independently of the oven with no temperature distribution in the separation column.

Also, according to the column module of the gas chromatograph device of the present invention, the separation column is accommodated inside the column accommodating member while being surrounded by the heat insulating member, and thus, the separation column is shut off from external air, and the temperature of the separation column may be prevented from being varied due to the influence of the convection or the temperature variation in the external air. The reproducibility of an analysis result is thereby increased. Moreover, since a gap for air to flow along the separation column is provided between the separation column and the heat insulating member, and the air inlet port for introducing the external air into the gap and the air outlet port for exhausting the air in the gap are further provided to the column accommodating member, at the time of cooling the separation column, the external air is introduced into the column module and the external air can flow through the gap between the column accommodating member and the separation column, the cooling efficiency of the separation column may be increased. Then, at the time of raising the temperature of the separation column, the temperature of the separation column may be swiftly raised due to the effect of being shut off from the external air by the heat insulating member, and at the time of cooling the separation column, the separation column may be swiftly cooled due to the effect of the external air flowing along the separation column, and thus, the wait time caused by the temperature adjustment for the separation column may be reduced, and the processing efficiency of an analysis operation is increased.

EMBODIMENTS OF THE INVENTION

According to a gas chromatograph device of the present invention, a column module may further include, on one of an air inlet port side and an air outlet port side, a fan for introducing cooling air into a gap from the air inlet port. Cooling air may then be introduced efficiently into the gap between a separation column and a heat insulating material, and the cooling efficiency of the separation column may be increased.

In the above-described case, the fan is desirably provided on the air inlet port side, and an air duct is desirably provided between the fan and the air inlet port. External air may then be introduced efficiently into the gap between the separation column and the heat insulating material.

In the column module of the gas chromatograph device of the present invention, a heater and the separation column may be integrally formed while being in contact with each other to thereby form a column temperature adjustment body, and a gap may be provided between the heat insulating member and the upper surface of the column temperature adjustment body and between the heat insulating member and the lower surface of the column temperature adjustment section. Then, since the cooling air introduced from the air inlet port flows over the upper surface and the lower surface of the column temperature adjustment body, the cooling efficiency of the separation column is further increased.

A plate heater may be cited as the heater for heating the separation column. In this case, the separation column is fixed while being in contact with one surface of the plate heater. The inside of the column module may thereby be heated with high efficiency.

A plurality of column modules may be held by the oven. For example, by installing and serially connecting two or more column modules having separation columns with different separation properties, a component which is not separated by one separation column may be separated by another separation column and be lead to a detector.

Hereinafter, a preferred embodiment of the gas chromatograph device will be described with reference to the drawings.

First, with reference to FIGS. 1A and 1B, a column module provided to the gas chromatograph device will be described.

A column module 2 is configured by having a column temperature adjustment body 3 accommodated inside a column accommodating member 10. The column accommodating member 10 is a cuboid member, and is configured from an outer wall and heat insulating members 12 arranged on the inside of the wall. The outer wall of the column accommodating member 10 is formed of metal, such as a stainless steel (SUS 304), and the heat insulating members 12 are formed of, for example, glass wool. An opening 16 is provided to one end of the column accommodating member 10, and an opening 18 is provided to the other end. A cavity 14 is provided inside the column accommodating member 10, and the heat insulating members 12 surround the cavity 14 from above and below and on the sides other than the openings 16 and 18. The cavity 14 communicates from the opening 16 to the opening 18, and the air is enabled to flow through the column accommodating member 10.

The column temperature adjustment body 3 is arranged inside the cavity 14 surrounded by the heat insulating members 12. The column temperature adjustment body 3 is configured by having a chip-shaped separation column 4, which is formed from a flow channel substrate, sandwiched by, and integrated with, retaining plates 5 and 7 from above and below while being arranged on a plate heater 6. The retaining plate 5 is supported by bases 8 that are embedded in the heat insulating member 12 on the lower side of the cavity 14, while being separated from the heat insulating member 12. The heater 6, the separation column 4, and the retaining plate 7 are stacked in this order from bottom to top on the retaining plate 5. Additionally, in this embodiment, the bases 8 are arranged at positions corresponding to the four corners of the plate heater 6, but the bases 8 may take any form as long as a structure where air flows through the gap between the retaining plate 5 and heat insulating member 12 on the lower side, along the separation column 4 is achieved.

A through hole 19 communicating with one end of the separation column 4 and a through hole 23 communicating with the other end are provided to the retaining plate 7 of the column temperature adjustment body 3, and an inlet port 20 connected to the one end of the separation column 4 via the through hole 19 and an outlet port 22 connected to the other end of the separation column 4 via the through hole 23 are provided to the upper surface of the retaining plate 7. The inlet port 20 is provided to connect a capillary (pipe) from a sample injection part for injecting a sample gas, and the outlet port 22 is provided to connect a capillary communicating with a detector for detecting a sample component. The inlet port 20 and the outlet port 22 are extended to the opening 18 so as to enable connection of the capillaries from outside the column accommodating member 10.

A gap exists between the upper surface of the column temperature adjustment body 3 and the heat insulating member 12 on the upper side, and between the lower surface of the column temperature adjustment body 3 and the heat insulating member 12 on the lower side. Accordingly, external air may be introduced into the column accommodating member 10 from one of the openings 16 and 18, and be exhausted from the other opening after passing through the gaps between the column temperature adjustment body 3 and the heat insulating members 12.

Additionally, in the embodiment described above, the chip-shaped separation column 4, which is formed from a flow channel substrate, is used, but a capillary column may be used instead. In this case, instead of the plate heater 6, a heating wire may be wound around the capillary column and be used. As the plate heater 6, a mica heater, a rubber heater, or a ceramic heater, for example, may be used.

Next, another example of the column module provided to the gas chromatograph device will be described with reference to FIGS. 2A and 2B.

According to this column module 2a, a column temperature adjustment body 3a formed from a separation column 4a, a heater 6a, and retaining plates 5a and 7a has its upper surface held by ceramic arms 24, which are holding members, and is supported in mid-air inside a cavity 14a inside a column accommodating member 10a. The ceramic arms 24 are provided in such a way as to extend from end surface sides of the column accommodating member 10b toward the cavity 14a to thereby hold the column temperature adjustment body 3a at four corners.

As in the embodiment of FIGS. 1A and 1B, the cavity 14a is a space surrounded by heat insulating members 12a from above and below and on the sides other than openings 16a and 18a. The openings 16a and 18a are provided to both end surfaces of the column accommodating member 10a, and external air is allowed to pass through the cavity 14a. The retaining plate 7a includes a cutout portion 26 at one end, and an inlet port 20a and an outlet port 22a of the separation column 4 are provided at the cutout portion 26.

As in the example described with reference to FIGS. 1A and 1B, according to the structure described above, a gap as a ventilation path exists between the upper surface of the column temperature adjustment body 3a and the heat insulating member 12a on the upper side, and between the lower surface of the column temperature adjustment body 3a and the heat insulating member 12a on the lower side, and the external air introduced into the column accommodating member 10a from one of the openings 16a and 18a may be exhausted from the other opening after passing through the gaps between the column temperature adjustment body 3a and the heat insulating members 12a. The column temperature adjustment body 4a may thereby be cooled highly efficiently.

Figure 3:
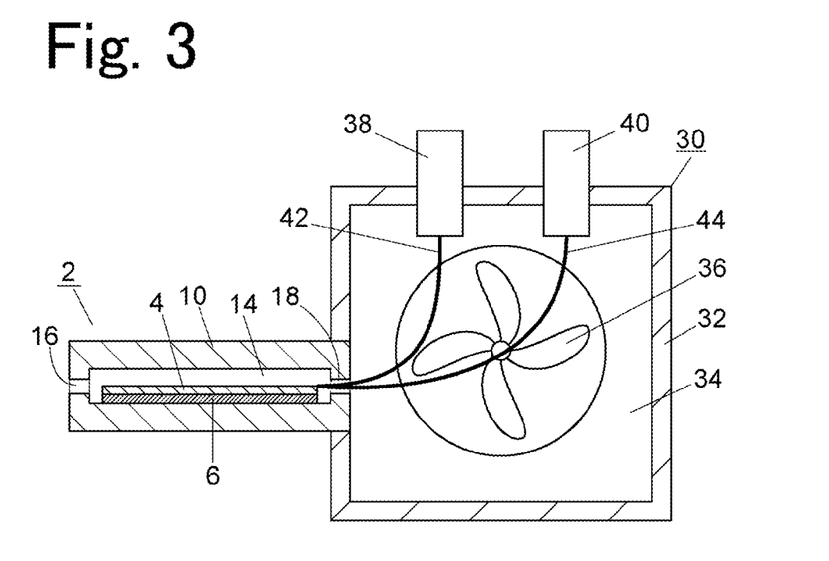
FIG. 3 is a cross-sectional diagram showing an embodiment of the gas chromatograph device.

An embodiment of the gas chromatograph device provided with the column module 2 in FIGS. 1A and 1B will be described with reference to FIG. 3. Additionally, FIG. 3 schematically shows the structure of the column module 2.

A sample injection part 38 and a detector 40 are attached to the upper surface of a housing 32 of an oven 30. Capillaries 42 and 44 are accommodated in an inner space 34 of the housing 32. The capillary 42 is for connecting the sample injection part 38 and the column module 2, and the capillary 44 is for connecting the column module 2 and the detector 40.

The column module 2 is attached to a side wall of the housing 32 of the oven 30. The column module 2 is fixed to the housing 32 of the oven 30 with the separation column 4 being horizontal in such a way that the end surface where the opening 18 is provided is on the side of the oven 30. An opening is provided to the side wall of the housing 32 where the column module 2 is mounted, and ends of the capillaries 42 and 44 are connected to the ports 20 and 22 of the column module 2 via the opening.

The oven 30 includes a heater (not shown) and a fan 36 inside the inner space 34 of the heat insulating housing 32, and controls the temperature of the inner space 34. The column module 2 performs temperature control of the separation column 4 independently of the oven 30. The column accommodating member 10 of the column module 2 has a structure where the cavity 14 inside is surrounded by the heat insulating materials 12, and thus, is able to control the temperature of the separation column 4 without being affected by the temperature variation or convection outside the column accommodating member 10. Since the heat capacity is lower than that of the oven 30, swift heating and cooling are enabled.

Cooling of the separation column 4 and the inside of the oven 30 is performed by exhausting the air inside the inner space 34 of the oven 30 by the fan 36 and reducing the pressure, and introducing external air into the inner space 34. Introduction of the external air into the inner space 34 is performed via the column module 2. That is, when the inner space 34 of the oven 30 is depressurized by the fan 36, the external air is introduced from the opening 16 of the column module 2, and is introduced into the inner space 34 from the opening 18 through the cavity 14 inside the column module 2. Accordingly, since the external air passes through the column module 2 with a low heat capacity, along the separation column 4, swift cooling of the separation column 4 is enabled. The opening 16 of the column module 2 forms the air inlet port for introducing the external air into the cavity 14, and the opening 18 forms the air outlet port for exhausting the external air from the cavity 14.

Figure 4:
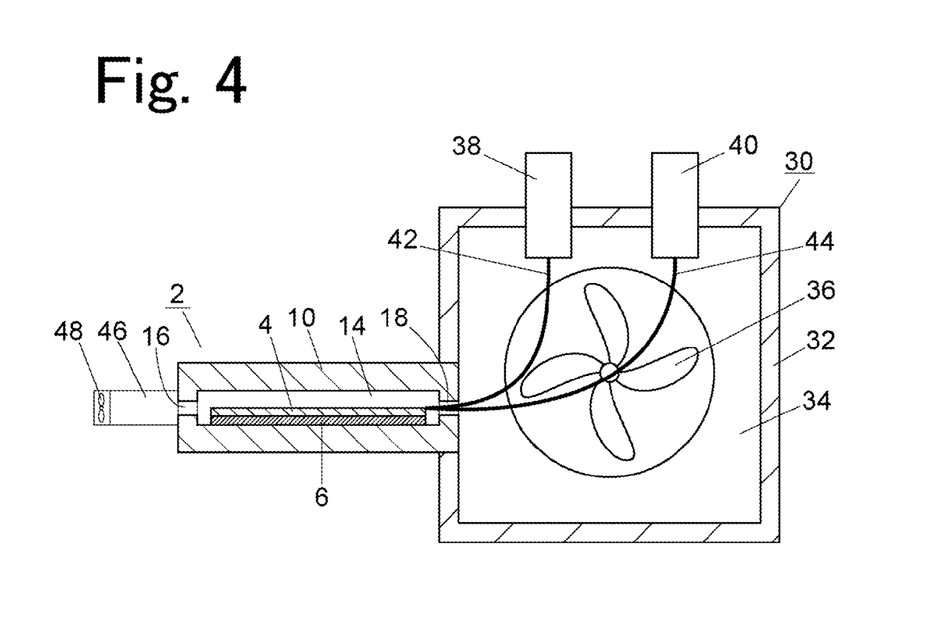
FIG. 4 is a cross-sectional diagram showing another embodiment of the gas chromatograph device.

As a method of further increasing the cooling efficiency of the separation column 4, providing a column fan 48 via an air duct 46 on the side of the opening 16 of the column module 2 may be cited as shown in FIG. 4. By sending the external air toward the column module 2 side by the column fan 48 at the time of cooling the separation column 4, the amount of cooling air that flows along the separation column 4 is increased, making it possible to cool the separation column 4 swiftly.

Additionally, in the embodiments of FIGS. 3 and 4, the column module 2 is mounted to the oven 30 with the separation column 4 being horizontal (hereinafter "horizontally placed"), and thus, temperature distribution is less likely to occur inside the column module 2, and the temperature of the separation column 4 may be uniformly controlled on the main plane. If the column module 2 is arranged with the separation column 4 perpendicularly placed (hereinafter "vertically placed"), temperature distribution in the vertical direction occurs inside the column module 2 due to thermal convection, and it becomes difficult to uniformly control the temperature of the separation column 4.

Figure 5:
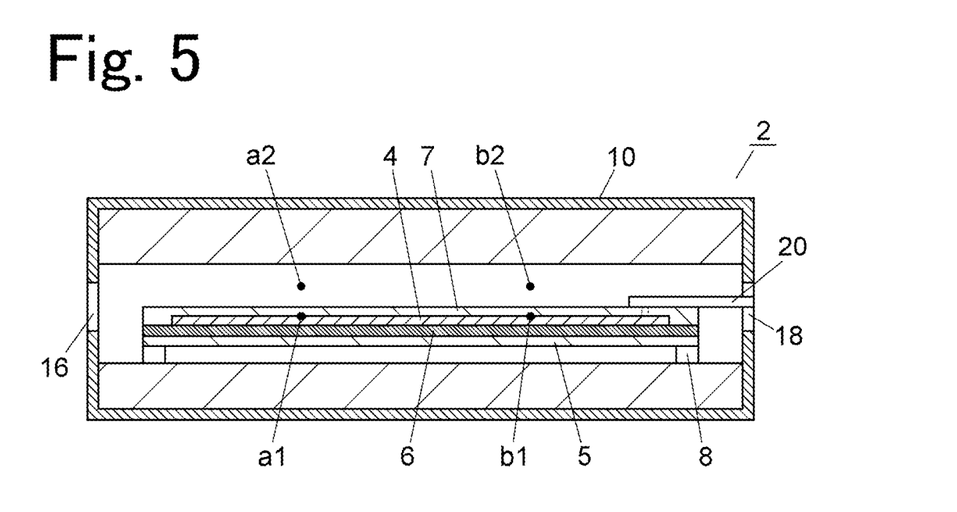
FIG. 5 is a cross-sectional diagram for describing temperature measurement points of the column module.
Figure 6:
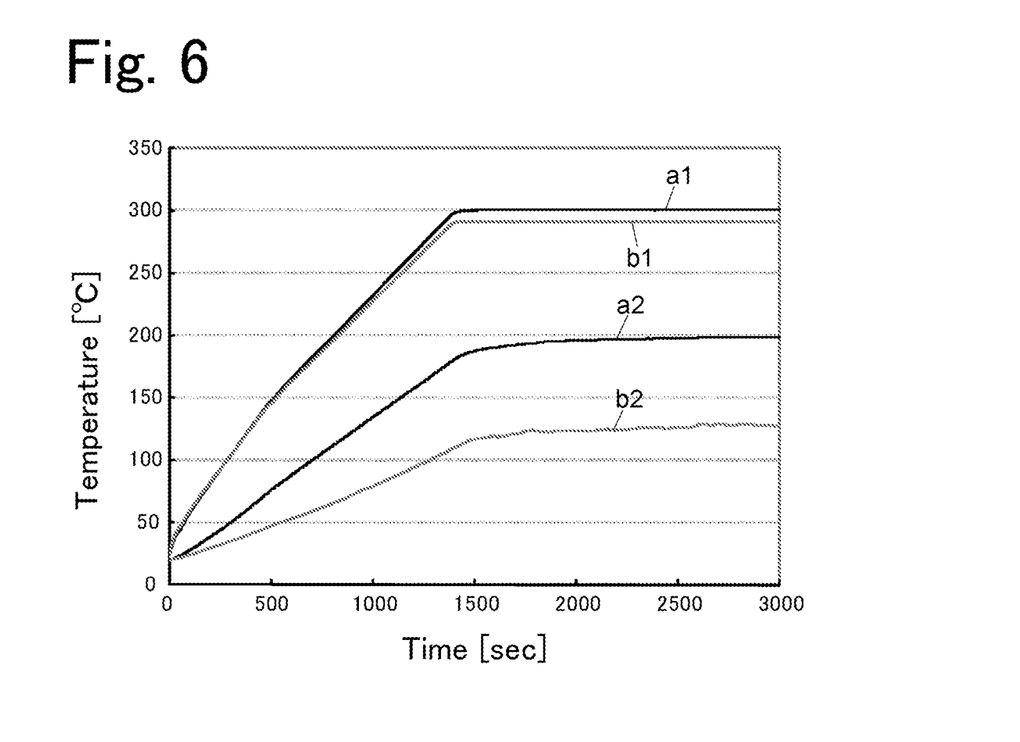
FIG. 6 is a graph showing a change over time of the temperature at each measurement point where temperature adjustment is performed with the column module perpendicularly arranged.
Figure 7:
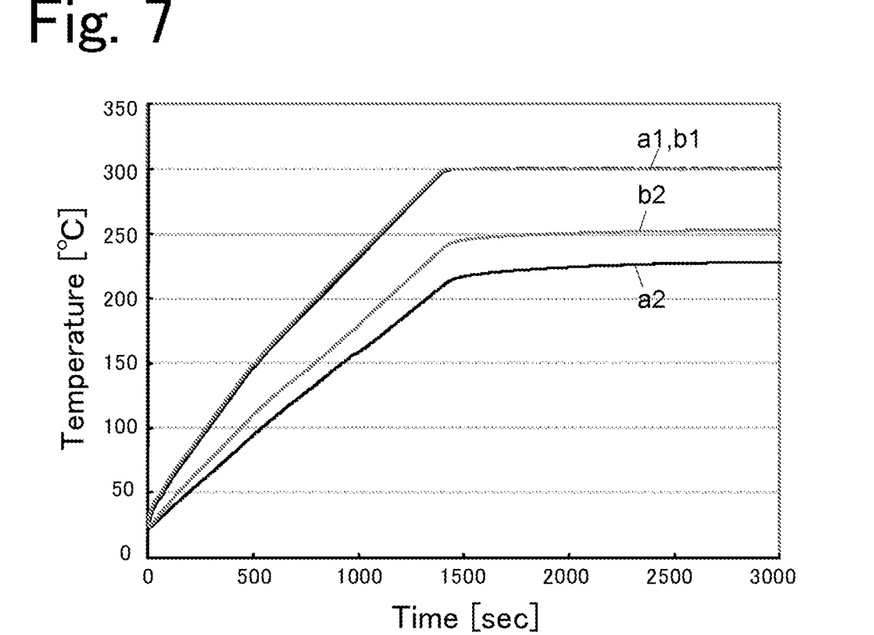
FIG. 7 is a graph showing a change over time of the temperature at each measurement point where temperature adjustment is performed with the column module horizontally arranged.

Data of changes over time of the temperature inside the column module 2 is shown in FIGS. 6 and 7. FIGS. 6 and 7 show changes over time of the measured temperature where the column module 2 is vertically placed and where the column module 2 is horizontally placed, respectively. As shown in FIG. 5, measurement of the temperature was performed by inserting thermocouples at a position a1 20 mm away from one end of the separation column 4, a position a2 in the nearby air space, a position b1 20 mm away from the other end of the separation column 4, and a position b2 in the nearby air space. The gap between a1 and a2 is 60 mm.

Comparing FIGS. 6 and 7, it can be seen that, when the column module 2 is vertically placed, there is a temperature difference between the positions a1 and b1, and between a2 and b2 even after sufficient time has passed from the start of heating by the heater 6 and the temperature has stabilized, but when the column module 2 is horizontally placed, there is no temperature difference between the positions a1 and b1, and the temperature difference between the positions a2 and b2 is small. In this manner, by placing the column module 2 horizontally, the temperature distribution inside the column module 2 is improved, and the temperature of the separation column 4 may be uniformly controlled.

Figure 1A:
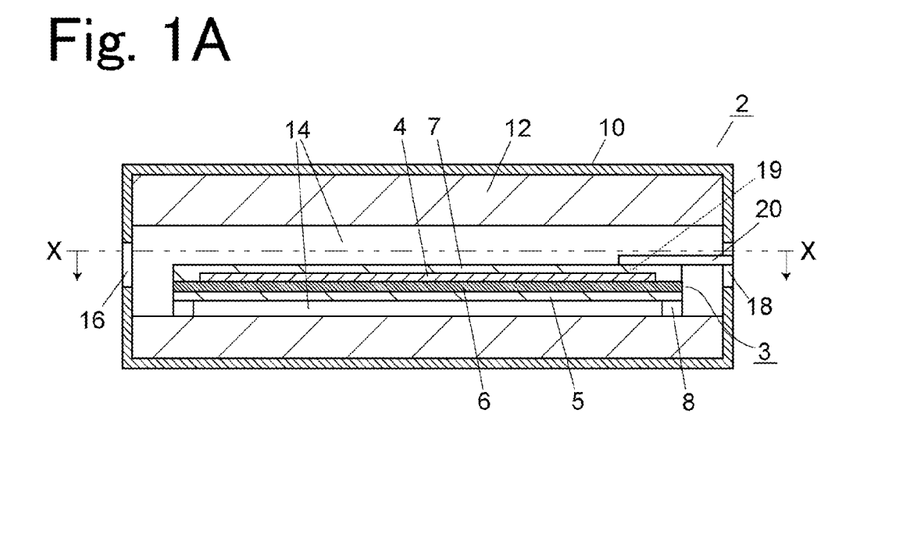
FIG. 1A is a cross-sectional diagram obtained by vertically cutting at the position Y-Y in FIG. 1B showing an example of a column module provided to a gas chromatograph device.
Figure 1B:
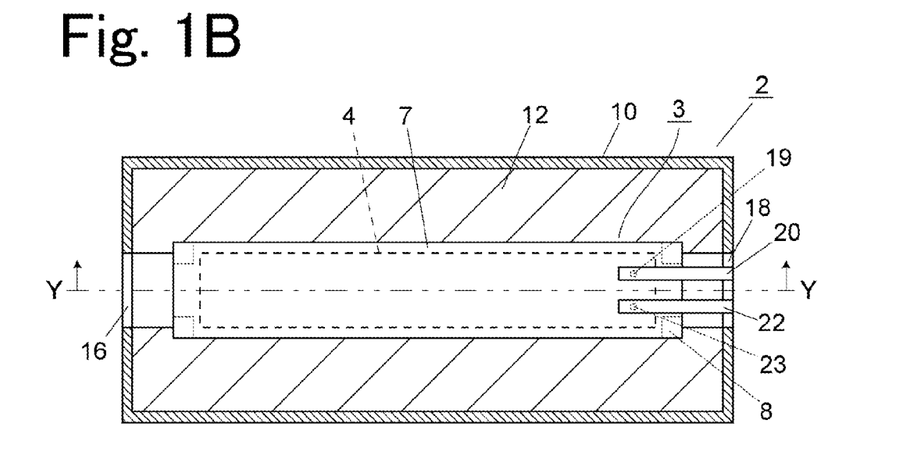
FIG. 1B is a cross-sectional diagram obtained by horizontally cutting the column module at the position X-X in FIG. 1A.
Figure 2A:
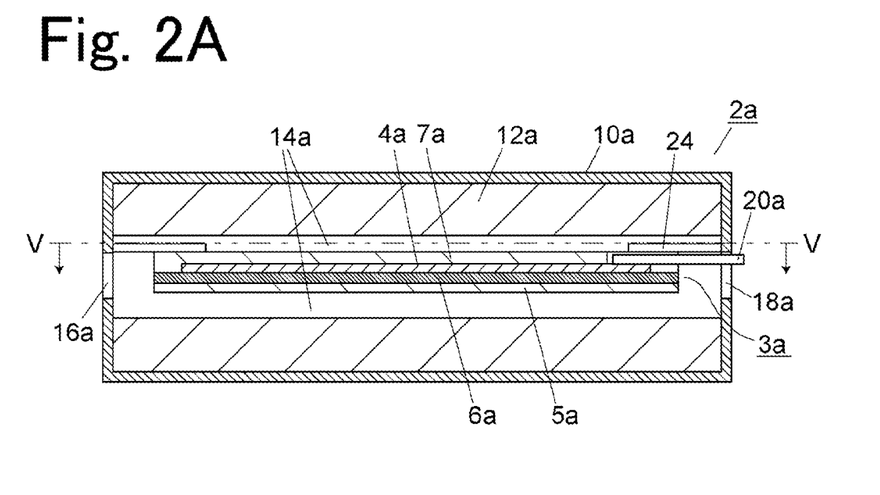
FIG. 2A is a cross-sectional diagram obtained by vertically cutting at the position W-W in FIG. 2B showing another example of the column module provided to the gas chromatograph device.
Figure 2B:
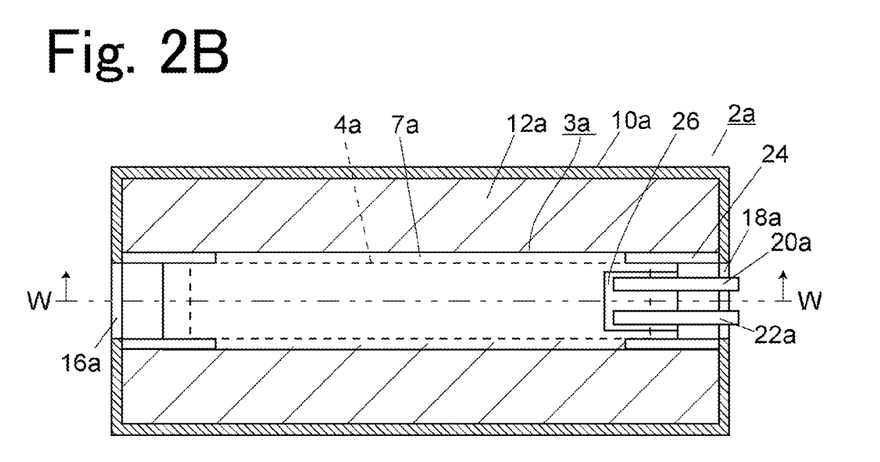
FIG. 2B is a cross-sectional diagram obtained by horizontally cutting the column module at the position V-V in FIG. 2A.

Additionally, the gas chromatograph devices in FIGS. 3 and 4 are provided with the column module 2 in FIGS. 1A and 1B, but the column module 2a in FIGS. 2A and 2B may alternatively be provided.

In the embodiment in FIG. 3, one column module 2 is mounted to the oven 30, but the present invention is not restricted thereto, and two or more column modules 2 may alternatively be mounted to the oven 30.

Figure 8:
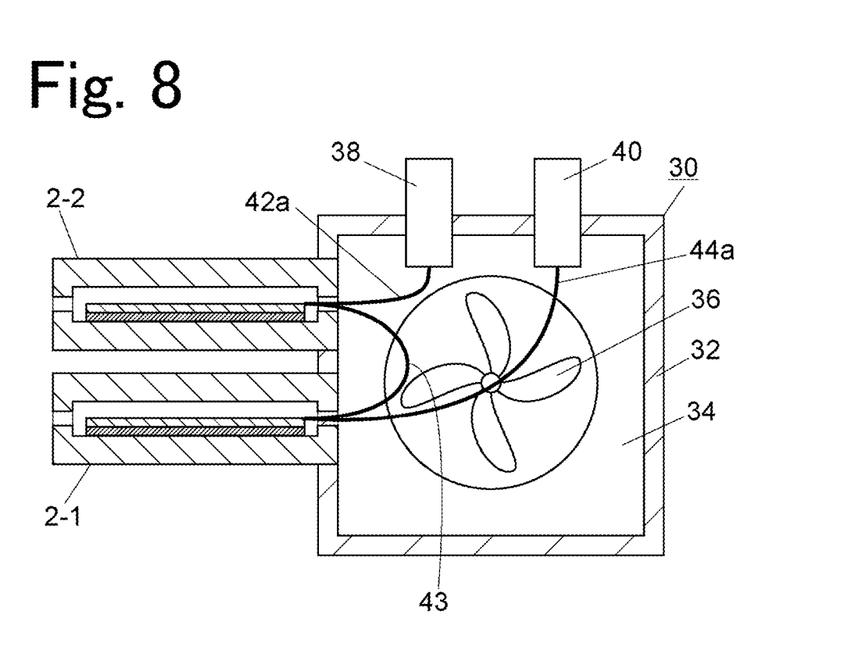
FIG. 8 is a cross-sectional diagram showing further another embodiment of the gas chromatograph device.

FIG. 8 shows an embodiment of a gas chromatograph device where a plurality of column modules are held by an oven. Two column modules 2-1 and 2-2 are mounted to the oven 30 in parallel with each other with their separation columns 4 being horizontal. The column modules 2-1 and 2-2 are serially connected. A sample injection part 38 is connected to an inlet port of the column module 2-1 via a capillary 42a. An outlet port of the column module 2-1 and an inlet port of the column module 2-2 are connected via a capillary 43. The outlet port of the column module 2-2 is connected to a detector 40 via a capillary 44a. Additionally, the column modules 2-1 and 2-2 of this embodiment may be the column module 2 in FIGS. 1A and 1B, or the column module 2a in FIGS. 2A and 2B.

DESCRIPTION OF REFERENCE SIGNS

2: Column module
4: Separation column
5, 5a, 7, 7a: Retaining plate
6, 6a: Heater
8, 8a: Support member
10, 10a: Column accommodating member
12, 12a: Heat insulating member
14, 14a: Gap
16, 16a: Air inlet port
18, 18a: Air outlet port
20, 20a: Column inlet port
22, 22a: Column outlet port
24: Ceramic arm
26: Cutout portion
30: Oven
32: Oven housing
34: Oven inner space
36: Oven fan
38: Sample injection part
40: Detector
42, 44: Capillary
46: Air duct
48: Column cooling fan

What is claimed is:

1. A gas chromatograph device comprising:
a column module including,
a column temperature adjustment body integrally formed from a chip shaped separation column for separating a sample gas into components and a plate heater for heating the chip shaped separation column by being in contact with each other, wherein the chip shaped separation column is fixed while being in contact with one plane of the plate heater, wherein the chip shaped separation column has a longitudinal direction,
a column accommodating member accommodating inside of which the column temperature adjustment body while surrounding the column temperature adjustment body by a heat insulating member, and including a gap for air to flow along the column temperature adjustment body between an upper surface of the column temperature adjustment body and the heat insulating member and between a lower surface of the column temperature adjustment body and the heat insulating member,
an air inlet port, provided at one end face of the column accommodating member, for introducing external air into the gap, the air inlet port facing one end of the chip shaped separation column in the longitudinal direction thereof, wherein the one end face is perpendicular to the one plane of the plate heater, and
an air outlet port, provided at an opposite side end face to the one end face of the column accommodating member, for exhausting air in the gap, the air outlet port facing the other end of the chip shaped separation column in the longitudinal direction thereof,
a sample injection part for injecting a sample gas into the separation column of the column module;
a detector for detecting a sample component separated by the separation column; and
an oven accommodating first and second flow channels, the first flow channel connecting the sample injection part and the chip shaped separation column, the second flow channel connecting the detector and the chip shaped separation column, the oven being for adjusting an internal temperature to a constant temperature, wherein the chip shaped separation column has inlet and outlet ports connected to the first and second flow channels accommodated in the oven, respectively, the inlet and outlet ports each protrude out of the air outlet port of the column module.

2. The gas chromatograph device according to claim 1, wherein the column module further includes, on a side of one of the air inlet port and the air outlet port, a fan for introducing cooling air into the gap from the air inlet port.

3. The gas chromatograph device according to claim 2, wherein the fan is provided on the side of the air inlet port, and an air duct is provided between the fan and the air inlet port.

4. The gas chromatograph device according to claim 1, wherein a plurality of the column modules are held by the oven.

5. The gas chromatograph device according to claim 1, wherein the column module is held by the oven with the chip shaped separation column horizontally arranged.

6. The gas chromatograph device according to claim 1, wherein the oven has a hole receiving the air outlet port of the column module for the attachment thereof.

7. A column module comprising:
a column temperature adjustment body integrally formed from a chip shaped separation column for separating a sample gas into components and a plate heater for heating the chip shaped separation column by being in contact with each other, wherein the chip shaped separation column is fixed while being in contact with one plane of the plate heater, wherein the chip shaped separation column has a longitudinal direction,
a column accommodating member accommodating inside of which the column temperature adjustment body while surrounding the column temperature adjustment body by a heat insulating member, and including a gap for air to flow along the column temperature adjustment body between an upper surface of the column temperature adjustment body and the heat insulating member and between a lower surface of the column temperature adjustment body and the heat insulating member, an air inlet port, provided at one end face of the column accommodating member, for introducing external air into the gap, the air inlet port facing one end of the chip shaped separation column in the longitudinal direction thereof, wherein the one end face is perpendicular to the one plane of the plate heater, and an air outlet port, provided at opposite side end face to the one end face of the column accommodating member, for exhausting air in the gap, the air outlet port facing the other end of the chip shaped separation column in the longitudinal direction thereof, wherein the chip shaped separation column has inlet and outlet ports connected to first and second flow channels accommodated in an oven, respectively, the inlet and outlet ports each protrude out of the air outlet port of the column module, the first flow channel connecting a sample injection part and the chip shaped separation column, the second flow channel connecting a detector and the chip shaped separation column, the oven being for adjusting an internal temperature to a constant temperature.

\* \* \* \* \*